(12) United States Patent
Ferris et al.

(10) Patent No.: US 6,275,723 B1
(45) Date of Patent: Aug. 14, 2001

(54) METHOD AND APPARATUS FOR PERFORMING NEUROIMAGING

(75) Inventors: Craig F. Ferris, Holden; Jean A. King, Worc; Arthur C. Allard, Templeton, all of MA (US)

(73) Assignee: Insight Neuroimaging Systems, Inc., Worcester, MA (US)

( * ) Notice: Subject to any disclaimer, the term of this patent is extended or adjusted under 35 U.S.C. 154(b) by 0 days.

(21) Appl. No.: 09/169,602

(22) Filed: Oct. 9, 1998

Related U.S. Application Data

(63) Continuation-in-part of application No. 09/073,546, filed on May 6, 1998, now abandoned.

(51) Int. Cl.[7] ................................................. A61B 5/055
(52) U.S. Cl. ......................... 600/417; 600/422; 324/318
(58) Field of Search ................................. 600/410, 417, 600/421, 422, 415; 606/130; 324/309, 318

(56) References Cited

U.S. PATENT DOCUMENTS

| | | | |
|---|---|---|---|
| 1,093,112 | * 4/1914 | Clarke et al. | 606/130 |
| 4,256,112 | 3/1981 | Kopf et al. | 128/303 |
| 4,534,050 | 8/1985 | Smith | 378/81 |
| 4,602,622 | 7/1986 | Bär et al. | 128/303 |
| 4,617,925 | 10/1986 | Laitinen | 128/303 B |
| 4,634,980 | * 1/1987 | Misic et al. | 324/322 |
| 4,638,798 | 1/1987 | Sheldon et al. | 128/303 B |
| 5,154,723 | 10/1992 | Kubota et al. | 606/130 |
| 5,281,232 | 1/1994 | Hamilton et al. | 606/130 |
| 5,311,868 | 5/1994 | Carbini et al. | 128/653.5 |
| 5,311,882 | 5/1994 | Gagne et al. | 128/845 |
| 5,330,485 | 7/1994 | Clayman et al. | 606/130 |
| 5,370,117 | * 12/1994 | McLaurin, Jr. . | |
| 5,388,580 | 2/1995 | Sullivan et al. | 128/653.1 |
| 5,531,229 | 7/1996 | Dean et al. | 128/866 |
| 5,588,430 | 12/1996 | Bova et al. | 128/635.1 |
| 5,595,191 | * 1/1997 | Kirk . | |
| 5,601,570 | 2/1997 | Altmann et al. | 606/130 |
| 5,681,326 | * 10/1997 | Lax | 606/130 |
| 5,738,045 | 4/1998 | Bleacher | 119/751 |
| 5,782,765 | * 7/1998 | Jonkman | 600/424 |
| 5,797,924 | 8/1998 | Schulte et al. | 606/130 |
| 5,800,353 | 9/1998 | McLaurin, Jr. | 600/407 |
| 5,836,878 | * 11/1998 | Mock et al. | 600/415 |
| 5,887,074 | * 3/1999 | Lai et al. | 382/128 |
| 6,138,302 | * 10/2000 | Sashin et al. | 5/600 |

OTHER PUBLICATIONS

"Functional MRI Using Awake Animal: Brain Activity Induced by Drinking" by E. Tabuchi, H. N. Mallick, T. Kondoh, T. Ono, and K. Torii, Dept. of Physiology, Toyama Med. & Pharm. Univ. Abstract of conference paper published in the Journal of Physiology, vol. 45, Suppl. 1, 1995.

T. Kamiryo, S. S. Berr, K. S. Lee, N. F. Kassell, and L. Steiner, "Enhanced Magnetic Resonance Imaging of the Rat Brain Using a Stereotactic Device with a Small Head Coil: Technical Note," Acta Neurochir (Wien) 133:87–92 (1995).

* cited by examiner

*Primary Examiner*—Marvin M. Lateef
*Assistant Examiner*—Shawna J. Shaw
(74) *Attorney, Agent, or Firm*—Hamilton, Brook, Smith & Reynolds, P.C.

(57) ABSTRACT

The present invention relates to a restraining assembly used in neuroimaging of animals in magnetic resonance imaging (MRI) systems. The body of the animal under study is secured within a tube with a head holder to reduce motion artifacts, particularly when the animal is awake. The tube is placed in the bore of the MRI system to conduct imaging procedures with a radio frequency coil adjacent to the animals' head.

18 Claims, 9 Drawing Sheets

METHOD AND APPARATUS FOR PERFORMING NEUROIMAGING

RELATED APPLICATION

This application is a C-I-P of U.S. patent application No. 09/073,546, filed May 6, 1998 and abandoned Mar. 27, 2000, and said patent aapplication is incorporated herein by reference.

FIELD OF THE INVENTION

The present invention relates to magnetic resonance imaging, and more particularly to a method and apparatus for performing functional magnetic resonance imaging (fMRI) in animals.

BACKGROUND OF THE INVENTION

Human studies utilizing functional magnetic resonance imaging (fMRI) have advanced our understanding of the regional and functional interplay between populations of neurons serving sensory, integrative and motor functions.

Changes in neuronal activity are accompanied by specific changes in hemodynamic functions such as cerebral blood flow, cerebral blood volume, and blood oxygenation. fMRI has been used to detect these physiologically induced changes in response to visual stimulation, somatosensory activation, motor tasks, and cognitive activity. During cognitive activity, the blood flow into the active region of the brain increases considerably compared with the tissue oxygen uptake which results in an increase in blood oxy-hemoglobin ($HbO_2$) content. The susceptibility difference between diamagnetic oxy-hemoglobin and paramagnetic deoxy-hemoglobin (Hb) creates local magnetic field distortions that cause a dispersion in the processional frequency of the water protons and a concomitant change in the magnetic resonance (MR) signal intensity which is proportional to the ratio of $HbO_2$ to Hb. These signal-intensity alterations related to blood oxygenation are termed the BOLD (blood oxygenation-level-dependent) effect. The voxels in which paramagnetic Hb content is decreased are illuminated in the image.

Unfortunately, extending these studies to animals has been difficult because technological limitations prevent restraining a conscious animal for prolonged periods of time in a magnetic resonance imaging (MRI) instrument. As a result most studies to date have been limited to animals which are typically anesthetized in order to minimize motion artifacts. In the last 5 years over 7,000 full length publications on MRI in animals have been written without a single reference to an awake animal. The low level of arousal during anesthesia either partially or completely suppresses the fMRI response and has impeded fMRI application to the more physiologically relevant functions that have been noted in humans.

Significant challenges remain in utilizing MRI techniques in both humans and anesthetized animals. One problem encountered in human studies has been artifacts from head movements. Studies in humans using invasive head fixation has shown improved image quality over non-invasive fixation and absence of fixation. However, this fixation method limits the amount of research time available for human subjects. On the other hand, animal studies must be performed under anesthetized conditions due to indiscriminate movement of conscious animals. Since image resolution is a salient feature of fMRI, precautions to ensure improved image quality with minimized head movements are essential. In addition to head movement, it has been observed that any motion outside the field of view can obscure or mimic the signal from neuronal activation.

SUMMARY OF THE INVENTION

Applicant's method and apparatus overcomes the difficulties of performing fMRI on awake animals by utilizing a novel restraining assembly to eliminate movement artifacts and to map neuronal activation after exposure to sensorimotor stimulation in conscious animals. The significance of applicant's method of neuroimaging in awake animals will change current imagery of the brain from either a static (as seen with most neurochemical measurements) or a low activation dynamic system in an anesthetized state (as seen with current fMRI or positron emission tomography (PET) measurements) to a real-time three dimensional functioning unit.

A novel stereotaxic assembly has been developed that can immobilize the head and body of awake animals for several hours, without restricting respiratory physiological functioning. The apparatus allows for collection of a consistent pixel by pixel representation of the brain over several data acquisitions under various experimental conditions. Applicants have demonstrated fMRI signal changes associated with neuronal activation in response to footshock and during odor stimulation. Changes are measured in conscious animals with and without the use of contrast agents and are correlated with significant alterations in cerebral blood flow. Importantly, the information is obtained without animal sacrifice.

It has been found that the foregoing objects may be readily obtained in the novel stereotaxic non-magnetic restraining assembly to immobilize the head and body of awake animals for insertion into the tunnel bore of a magnetic resonance imaging assembly.

In a first embodiment of the invention, the assembly has a generally planar horizontal chassis with a front mounting plate and rear mounting plate extending perpendicular to the chassis and located adjacent to each end of the chassis. A body tube bracket also extends perpendicular to the chassis and is located between the front and rear mounting plates. The body tube bracket can be fastened (via aligning screws) at different locations along the chassis to accept different sized animals. The animal is placed in a body tube with its head in the circular aperture of a head holder. The body tube slides into a central access hole located in the approximate center of the rear mounting plate and the body tube bracket and is thereby attached to the chassis. The head holder fastens to the chassis between the body tube bracket and the front mounting plate.

The head holder restrains the head of the animal to prohibit vertical and horizontal movement of the animal during imaging. The head holder has a bite bar extending horizontally creating a chord along the bottom of its circular aperture. A vertical nose clamp extends through the top of the head holder and abuts the animal's nose to clamp the animal's mouth thereon.

The animal's head is further restrained by a pair of lateral ear clamping screws that extend horizontally through the sides of the head holder and a nose clamping screw that extends vertically through the head holder. A protective ear piece is placed over the animal's ears and receives the tips of the lateral ear clamping screws.

The head holder may be fitted with a radio frequency (rf) coil used to transmit rf radiation and receive the resulting MR signal.

A second embodiment of the invention has a general structure similar to the first embodiment with the following adaptations. The rear mounting plate has a removable crown to allow for simplified placement of the body tube into the rear mounting plate. In addition to the nose clamping screw as in the first embodiment, the means for restraining the head includes two additional bottom jaw anchor screws located below the bite bar and extending radially inward toward the circular access hole to secure the animal's lower jaw against the horizontal bite bar. A head clamping screw extending located to the rear of the nose clamp and extending radially inward is included to further secure the animal's head.

A further adaptation of the first embodiment includes a means of restraining an animal and prohibit limb movement. An animal is placed into a restraining jacket that is wrapped at the back to restrain the animal. Holders for the arms and legs further restrict the animal's movement. Soft rubber ear pads may be fitted into the ear canals to minimize any irritation to the area and mollify background noise.

Accordingly, it is an object of this invention to provide a new and useful method and apparatus for performing neuroimaging on awake animals.

It is a further object of this invention to provide a method and apparatus for stereotaxically restraining an awake animal to prevent movement while undergoing fMRI.

Yet another object of this invention is to provide a stereotaxic restraining assembly which is adaptable to different sized animals.

Another object of this invention is to amplify the sensitivity of low field strength magnets with the use of exogenous contrast agents, blood oxygenation-level-dependent contrast and radio frequency sequences.

A further object of this invention is to register into a three-dimensional digital map of the brain created from a computerized histological representation of fMRI data obtained from fMRI scans.

Further objects and advantages of the present invention will become apparent from a consideration of the drawings and ensuing description.

BRIEF DESCRIPTION OF THE DRAWINGS

With respect to the first embodiment.

Figure 13:
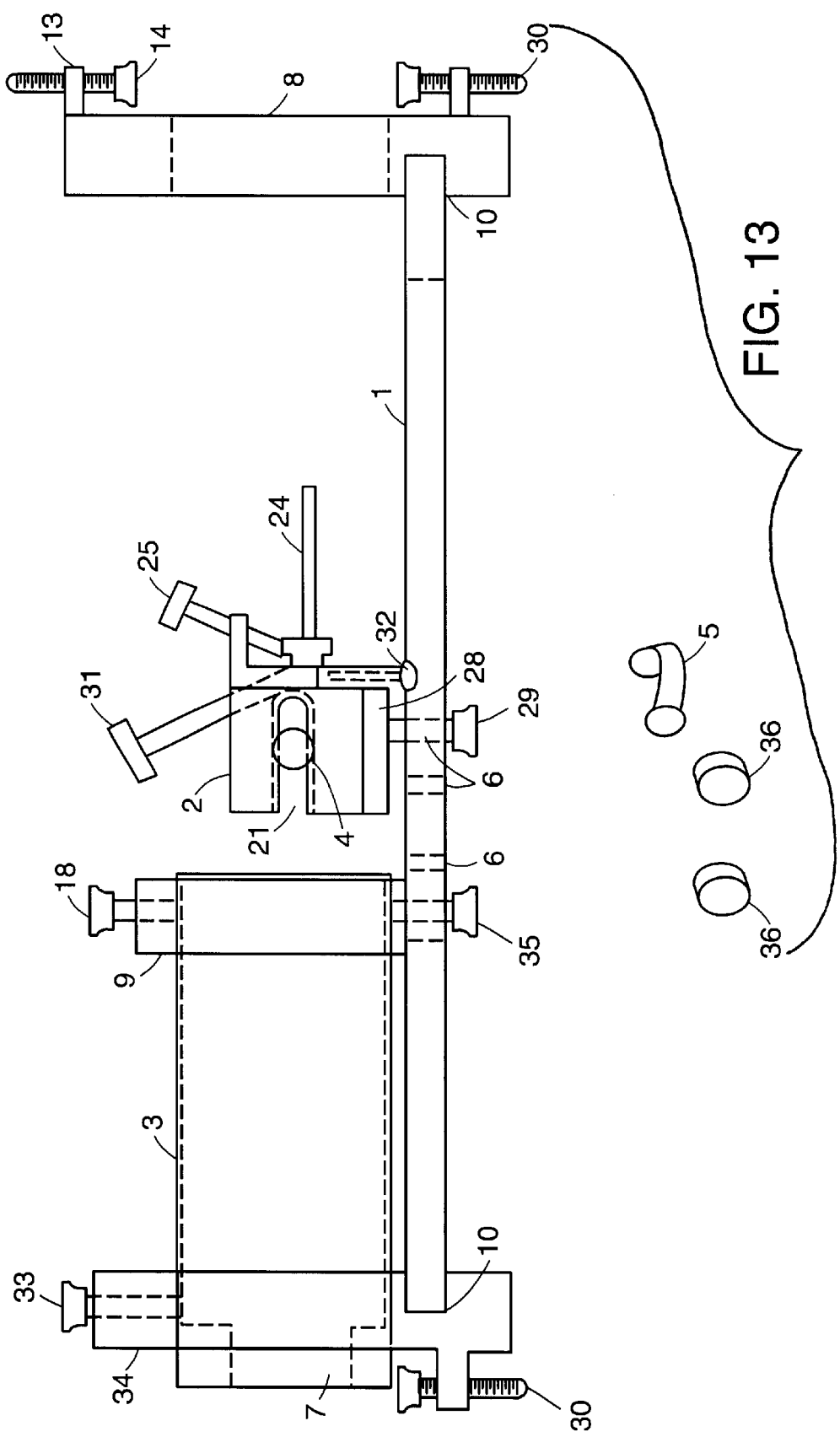
Figure 14:
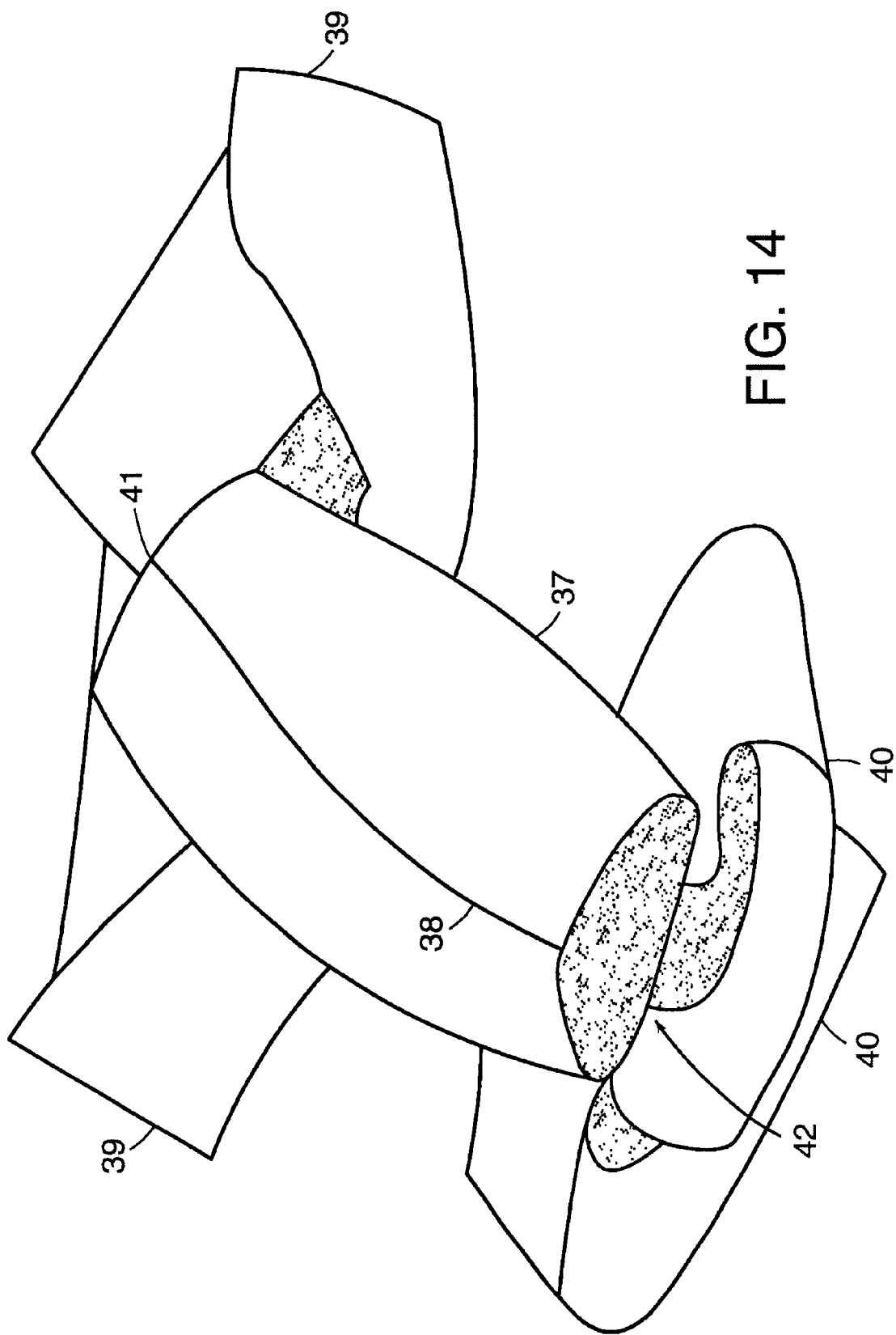

With respect to the second embodiment:

FIG. 13 is a side perspective view of the fMRI restraint assembly components;

FIG. 14 is a view of the restraining jacket.

DETAILED DESCRIPTION OF THE INVENTION

EXAMPLE I

To test the first embodiment of the invention, gold plated surface electrodes were attached to the skin of the right or left hindpaw of five male Sprague-Dawley rats (300–350 g) and connected to an electrical stimulator that provided 25 V pulses of 0.3 ms duration of 3 Hz (current of approximately 2.6 mA depending on skin resistance). Animals were lightly anesthetized with intra-peritoneal administration of chloral hydrate (300 mg/kg; Sigma, St. Louis, Mo.). The head was mounted and secured in a head holder custom fitted with a "birdcage" rf coil. The body of the animal was placed tightly into an animal holder, designed to allow for unrestricted respiration with lateral movement. Animals routinely recovered from the anesthesia within 30 min., as evidenced by tail withdrawal, hindlimb movement and occasional vocalizations. Blood pressure and heart rate were continuously monitored for signs of distress. The apparatus was inserted into the tunnel bore of a MRI device.

Magnetic resonance images were acquired using CSI-II 2.0T/45 cm imaging spectrometer (GE NMR Instruments, Fremont, Calif.) equipped with self-shielded gradient coils capable of producing a maximum field strength of ±20 G/cm. The image processing was performed off-line on a computer workstation (100 MHz Iris Indigo R4000 Silicon Graphics, Inc., Mountain View, Calif.) and analyzed on a Power MAC 610/66 using NIH image software (version 1.54). Prior to acquisition of the fMR images, a series of scout images were acquired with an eight-slice, echo-planar imaging (EPI) sequence (field-of-view), FOV=25.6×25.6 mm; 64×64 data matrix; 65 ms image acquisition window), to determine the exact position of the animal. Approximately 120 minutes after positioning the animal in the magnet, axial T2*-weighted, BOLD images of the rat brain (under resting and stimulated conditions) were acquired using a 2D gradient-echo imaging sequence (repetition time, TR=200 ms; echo time, TE=20 ms; 2-mm slice thickness; 128×128 data matrix). After a baseline study, the stimulus was applied for two minutes at 25 V and 1 minute at 10 V before data collection. The resulting stimulated and baseline images were subtracted to reveal regions of activation. The region of greatest activation on the contralateral (to stimulated hindpaw) somatosensory frontal and parietal cortices was integrated from the subtraction image by pixels ±2SD above the signal-to-noise threshold with computer-assisted tomography. The corresponding region of the baseline and stimulated datasets were demarcated and the relative signal intensity was calculated on a pixel-by-pixel basis.

BOLD-based signal intensity was correlated to hemodynamic changes through measurement of relative cerebral blood flow (rCBF) in the region of interest. A T2*-weighted, gradient-echo EPI sequence (TR=900 ms; TE=38 ms; 65 ms image acquisition window, number of signal averages, NEX=1) was used to acquire 25 images from the same slice which gave the maximum BOLD signal intensity changes. A bolus of contrast agent gadopentetate dimeglumine (0.15 ml) was administered after the seventh image. The change in the $T_2^*$ rate, $\Delta R_2^*(t)$=was obtained from the change in signal intensity based on the following relationship: $\Delta R_2^*(t)=1n[S(t)/S_o]/TE$ (where S(t) is the signal intensity at the time t). The relative cerebral blood volume (rCBV) and mean transit time (MTT) were determined for each pixel by the integration of $\Delta R_2^*$ (t) and an estimate of the first moment of t, respectively. The rCBF was determined, on a pixel-by-pixel basis, from the ratio of rCBV to MTT and rCBF maps were calculated from the 25 images. Since the cerebral hemodynamic state in a non-activated brain is quite stable over time, the resting-state rCBF maps were subtracted from the stimulated-state rCBF maps to create a new functional map depicting local changes caused by the hindpaw stimulation. Then the baseline and stimulated rCBF maps were anatomically correlated to BOLD-based images allowing for delineation of boundaries between the activated and the non-activated regions. The relative signal intensity was calculated, on a pixel-by-pixel basis, from the selected region.

Functional MRI can be performed in conscious animals provided that there is adequate restraint. The acquired images had minimal motion artifacts, even with maximum stimulus strength. The signal enhancement was related to stimulation intensity and was independent of which hindpaw was stimulated. For example, the increase in signal intensity with the 25 V stimulation was approximately 18% and with 100 V it increased to 30%. The activated regions can be clearly discerned in the subtraction images. The region of activation in individual animals varied in exact location and size since non-invasive skin electrodes (with large surface area) were used to minimize distress in the conscious animals.

Concurrent perfusion studies in the region identified by the BOLD technique showed corresponding increases in cerebral blood flow. An average local increase in rCBV of 67±15% and in rCBF of 64±8%, corresponding to the initial BOLD changes of 18±1% (mean ±SE, n=5), was observed. The subtraction images revealed good regional association between the activated cortical region measured for rCBF and BOLD signal changes, respectively. The average $1/T_2^*$ change of XXXX corresponding to BOLD change of XXXX (mean±SE, n=X) was measured in the region of interest.

Since this study was done on conscious animals, comparisons with similar studies are somewhat limited. However, the results of this study are consistent with a number of previous investigations. First, studies examining signal intensities in anesthetized animals post-stimulation range from 5% obtained at 2.0 Tesla (T) to 5–17% (peak voxels 30%) obtained at 7.0T magnet. The relatively large BOLD signal intensity changes observed in this study may be due to the increased neuronal activation status of conscious animals, compared to the anesthetized counterparts. In this case, however, comparisons of signal intensity changes between different studies can be misleading due to differences in image acquisition parameters and/or magnetic field strengths. To circumvent this problem, applicant has attempted to estimate the signal-intensity changes for our experimental conditions. In an in vivo study, Prielmeier et al. have determined $1/T_2^*$ rates of rat brain during hypoxia and interleaved normoxic phases (x). They found that $1/T_2^*$ increases in a linear manner with arterial deoxygenation. In the study, a mild and moderate deoxygenation (less than 40%) corresponds to an approximate change of 5.5 1/s in $1/T_2^*$. A severe deoxygenation (over 40%) has lead to a plateau, which authors expect to result from enhanced cerebral blood flow (X). In applicant's study, a change of XXX in $1/T_2^*$ was measured. Also, in an in-vitro study by Thulburn et al. (K. R. Thulburn, J. C. Waterton, P. M. Metthews, G. K. Radda, Biochemica et Biophysica Acta, 714, p. 265–270, 1982) a $1/T_2$ change of 8.3 $S^{-1}$ correlated with a 75% change in oxygenation at 1.9T (close to our 2.0T field strength). Third, in a static mathematical model, an approximate 60% change in blood oxygenation corresponded to a 64% increase in CBF at 1.50 level of CBV. Taken together, the above studies support the current quantitative data generated in conscious animals lining changes in BOLD and rCBF. Although one must be aware that extrapolation across differences in neuronal activation state (awake vs. anesthetized) and experimental parameters, as well as interspecies variations, may complicate more direct comparisons. Furthermore, other reported stimulus duration and intensity dependent phenomena like signal saturation and undershoot after stimulation period were observed in these studies.

EXAMPLE II

To test a second embodiment of the invention, an adult male marmoset was lightly anesthetized and fit into a custom-made cloth jacket to keep the arms and legs from being pulled forward. A plastic semicircular headpiece with blunted ear supports and soft rubber ear pads were fit into the ear canals to minimize any irritation to the area and mollify the sound of the radio frequency pulses. The marmosets head was placed into the cylindrical head restrainer with the animals canines secured over a bite bar and ears positioned stereotaxically inside the head restrainer with adjustable screws fit into lateral slits. The head holder was secured to the mounting unit with plastic screws. The body of the animal was placed into the body restrainer. The body restrainer was secured onto the mounting unit and the assembly was placed into the tunnel bore of a MRI device. (The marmoset generally awoke from anesthesia after approximately 45 to 60 minutes.) Magnetic resonance images were acquired on a General Electric CSI-II 2.0-T/45-cm bore imaging spectrometer equipped with self-shielded gradient coils capable of producing a maximum field strength of ±20 G/cm (General Electric Co., Fremont, Calif.). Prior to the experiment, the head restrainer is custom-fit with a birdcage radio frequency coil. These coils are used to transmit the rf radiation and receive the resulting MR signal. Radio frequency coils are usually custom-fitted to the desired anatomy to give maximum filling factor which results in optimal sensitivity. A prototype birdcage coil of 5.8 cm diameter by 4.4 cm in length was custom-fitted around the head holder. The circuitry was tuned to 85.557 MHz frequency.

There is a paucity of MRI data in non-human primates, hence it was necessary to collect a set of serial images focusing on the brain anatomy of the adult male marmoset. $T_1$-weighted anatomical images were acquired from three orthogonal planes using multi-slice spin-echo imaging sequence. Two sets of eight slices were acquired in an interleaved fashion, resulting in 16 continuous slices, each 2 mm thick. The repetition time (TR) of acquisitions (NA) was 2 and the digital resolution was 256×128.

Prior to acquisition of the fMR images, scout images from the three planes were acquired with a single slice, spin-echo sequence (FOV=50×50 cm, digital resolution of 256×128, NA=2), to determine the exact position of the animal's head. BOLD based fMRI data sets were acquired from rest, control and stimulated conditions using multi-slice gradient-echo sequence (TR=240 ms, TE=20 ms, NA=2, and digital resolution of 128×128). First, a series of baseline images were acquired to record background noise level and detect possible motion artifacts.

After baseline acquisitions were taken, data from the rest period for room air, stimulus scent (odor of a receptive female) and control scent were collected. At the onset of olfactory stimulation, a stimulus cup was opened and placed 1.2 cm from the nose of the marmoset. A fan was positioned at the back of the magnet pointing outward, pulling a gentle draft of air through the bore. After three minutes, the stimulus cup was removed, exposing the animal to room air for two minutes followed by a three minute period with the control cup. This sequence was repeated four times with a five minute rest period in between. Data was collected during stimulus and control exposures. When the stimulus cup was not in use, it was sealed. Two sets of images were acquired during each presentation of the scent.

The image processing was performed off-line on a 100 MHz HP Apollo 735 workstation using IDL imaging software, Version 4.0 and analyzed on a Power Mac 60/66 using NIH imaging software, Version 1.56 (Apple Computer, Inc., Cupertino, Calif.). The stimulated and baseline images were subtracted to reveal regions of activation. The region of greatest activation was determined from the subtraction image. The corresponding region of the baseline and stimulated data sets were demarcated and the relative signal intensity was calculated on a pixel-by-pixel basis. Brain activity increased with time of exposure to the scent of the receptive female.

DETAILED DESCRIPTION OF THE DRAWINGS

Figure 1:
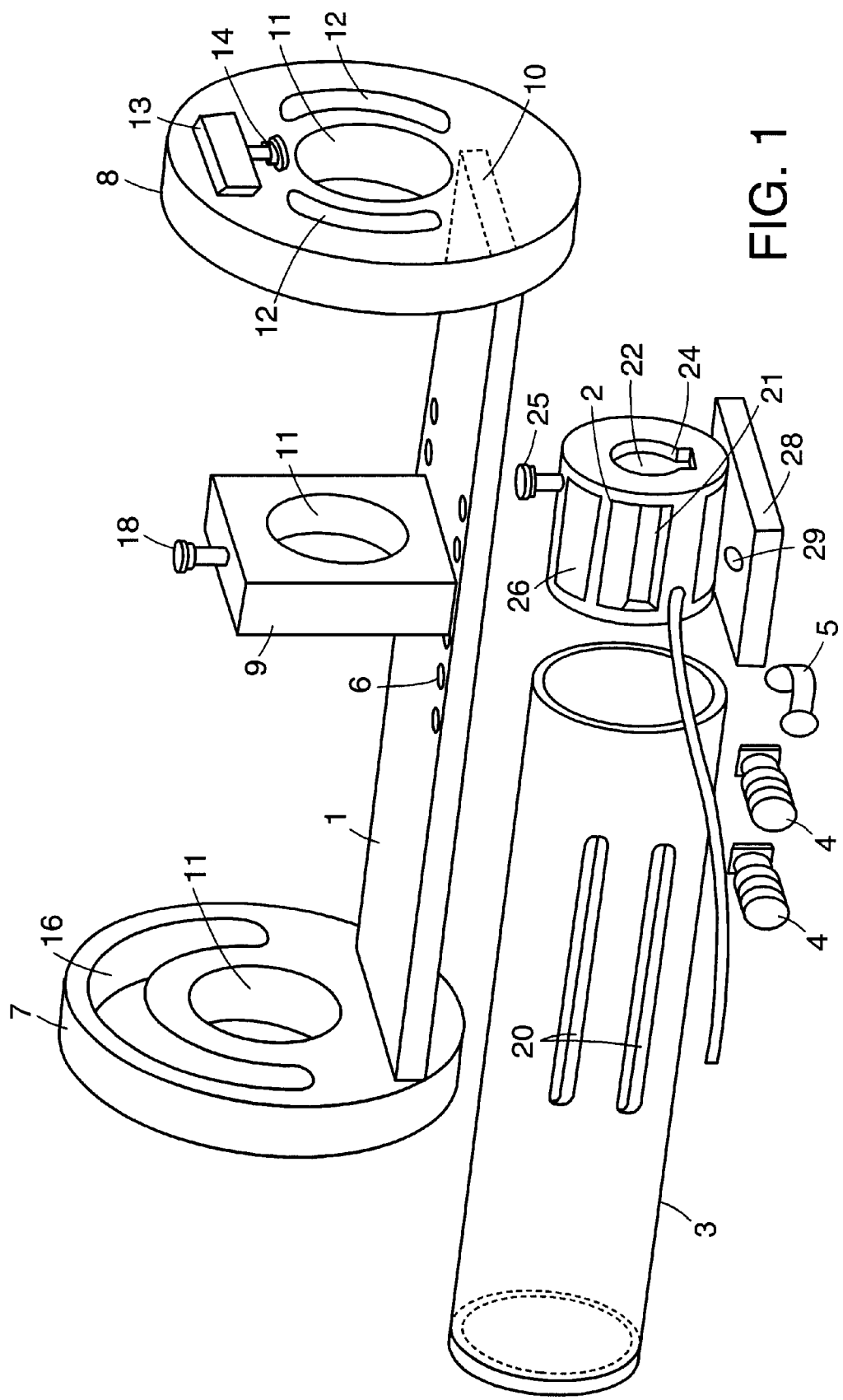
FIG. 1 is a side perspective of fMRI restraint assembly components.

Turning first to FIG. 1, therein illustrated is a disassembled fMRI restraining assembly having a Plexiglas™ chassis generally designated by the numeral 1, a Plexiglas™ cylindrical head holder generally designated by the numeral 2, a Plexiglas™ body tube generally designated by the numeral 3, a rear mounting plate generally designated by numeral 7, a front mounting plate generally designated by numeral 8, and a body tube bracket generally designated by numeral 9. One end of the chassis 1 is fitted into chassis mounting slot 10 (not shown) of rear mounting plate 7 and the opposite end of chassis 1 is fitted into chassis mounting slot 10 of the front mounting plate 8.

Figure 2:
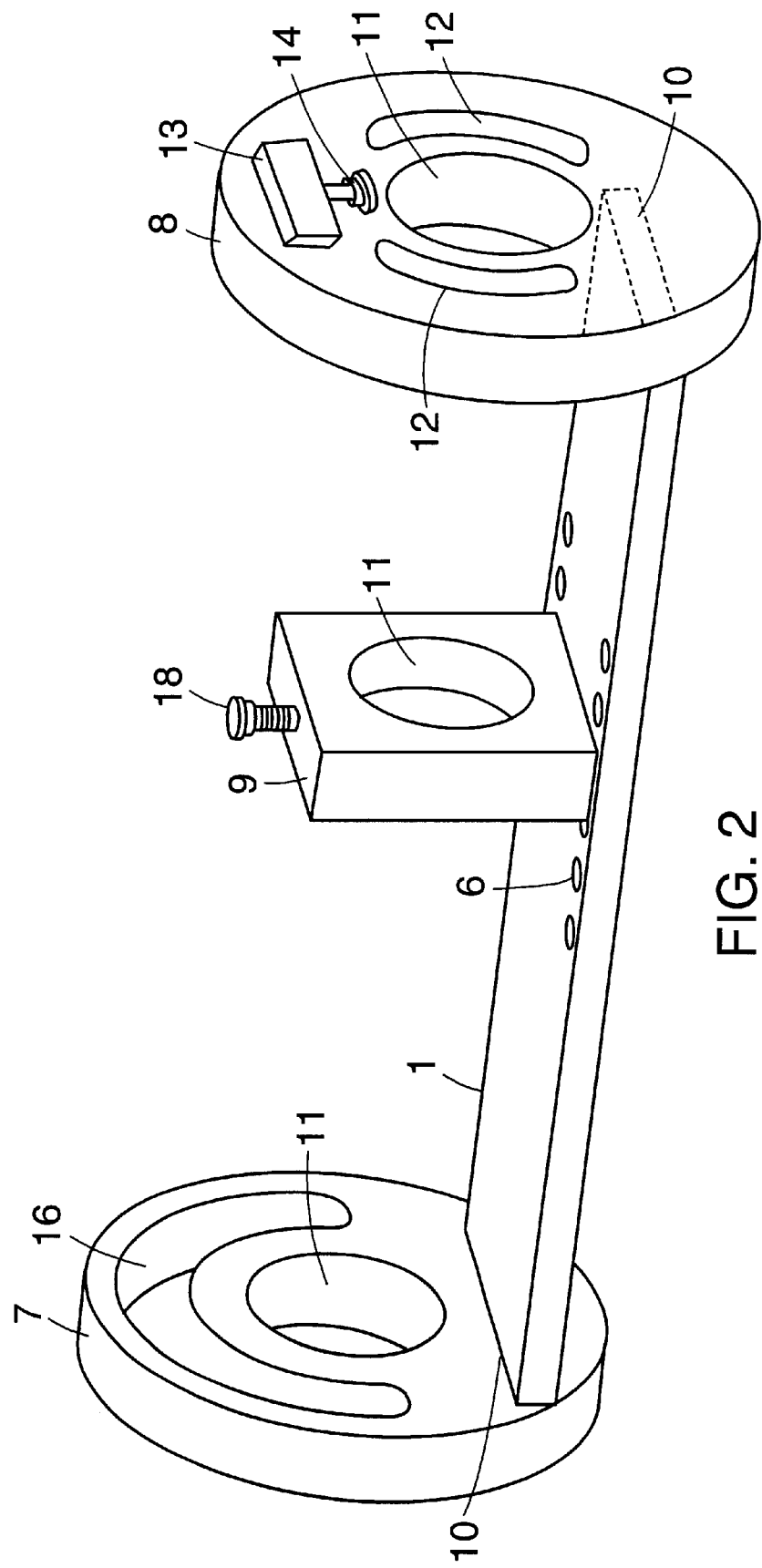
FIG. 2 is a side perspective view of the mounting unit.

Turning in detail to the assembly as seen in FIG. 2, therein is illustrated an elongated rectangular Plexiglas™ chassis 1 with a series of parallel opposing adjusting holes 6 drilled approximately midway therein. At one end of the chassis 1 is a circular Plexiglas™ rear mounting plate 7 and at the opposite end of the chassis is a circular Plexiglas™ front mounting plate 8. Also, shown in FIG. 2 is a square Plexiglas™ body tube bracket 9 adjustably mounted to the chassis 1 by a pair of screws 35 (shown in FIG. 13) extending through the chassis in the correlating mounting screw holes 6 and into body bracket tube 9.

Figure 3:
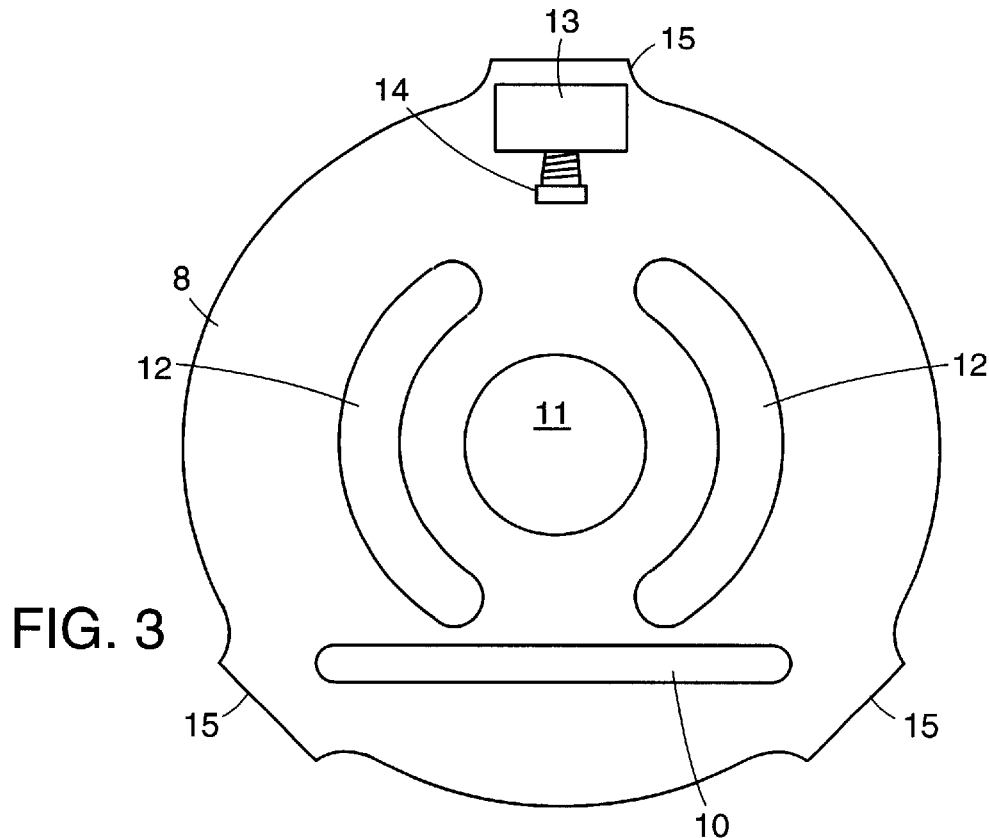
FIG. 3 is a front view of the front mounting plate.

FIG. 3 is a detailed view of the front mounting plate 8 having a centrally located circular access hole 11 extending through the approximate mid-section of the front mounting plate and a chassis mounting slot 10 extending horizontally below the circular access hole 11 which receives the chassis 1. Screw alignment slots 12 are located radially from the central circular access hole 11 to allow access through the front mounting plate 8 for adjustment of head holder 2. An assembly mounting block 13 and assembly mounting screw 14 penetrating the assembly mounting block 13 are located an outer surface of the front mounting plate 8 above the circular access hole 11 to secure the assembly in the cylindrical bore of a MRI tunnel (not shown). At radially equidistant points located on the perimeter of the front mounting plate 8 are three assembly centralizers 15 which provide further stability to the assembly when placed into the cylindrical bore of a MRI tunnel.

Figure 4:
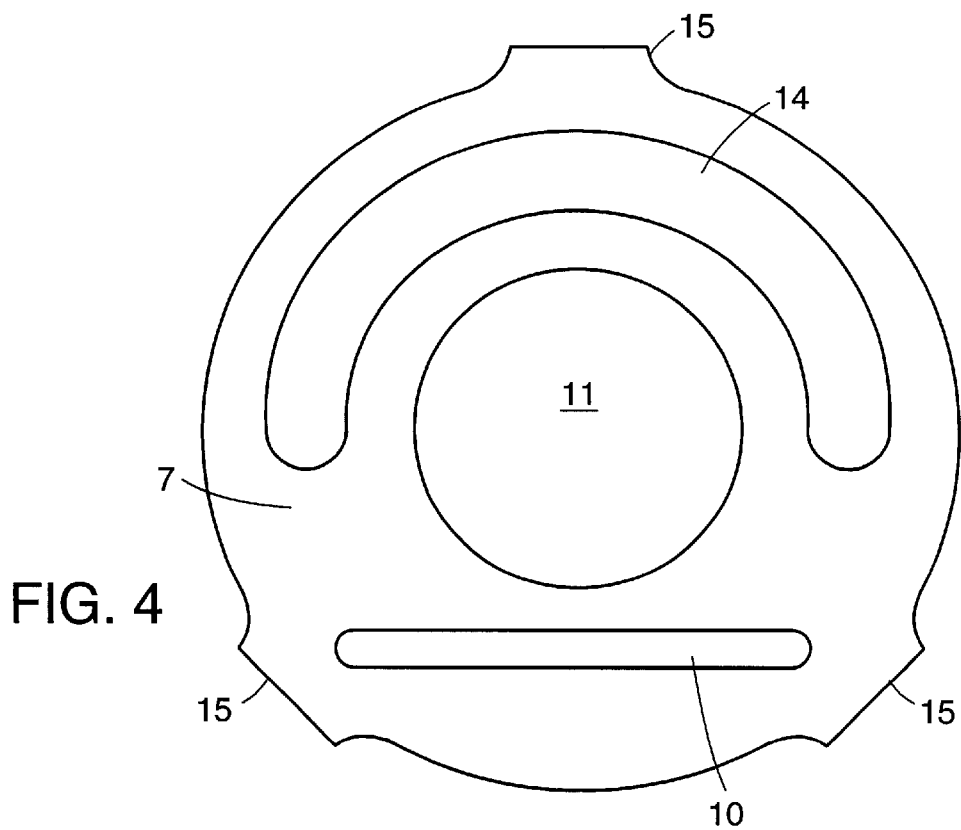
FIG. 4 is a front view of the rear mounting plate.

FIG. 4 shows a detailed view of the rear mounting plate 7 having a central circular access hole 11 and a horizontal chassis mounting slot 10 extending horizontally below the circular access hole 11 which receives the chassis 1. Arcuate cable access slot 16 is located above the access hole 11 to allow access through the rear mounting plate 7. At radially equidistant points located on the perimeter of the rear mounting plate are three assembly centralizers 15 provide further stability to the assembly when placed into the cylindrical bore of a MRI tunnel. Assembly centralizers 15 also act as feet to stabilize the assembly when it is free standing outside the cylindrical bore of a MRI tunnel.

Figure 5:
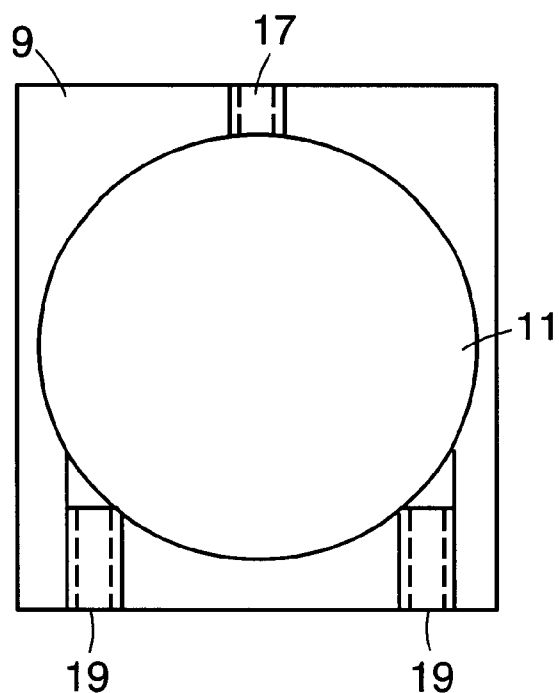
FIG. 5 is a front view of the body tube bracket.

FIG. 5 shows a detail of the body tube bracket 9 which has an access hole 11 therein for receiving the body tube 3 and a clamping screw hole 17 located through the top surface to receive a clamping screw 18 for temporarily fastening the body tube 3 to the body tube bracket 9. The bottom surface of the body tube bracket 9 has a pair of threaded mounting screw holes 19 for receiving aligning screws 35 (shown in FIG. 13) which detachably attach the body tube bracket 9 to the chassis 1.

Figure 6:
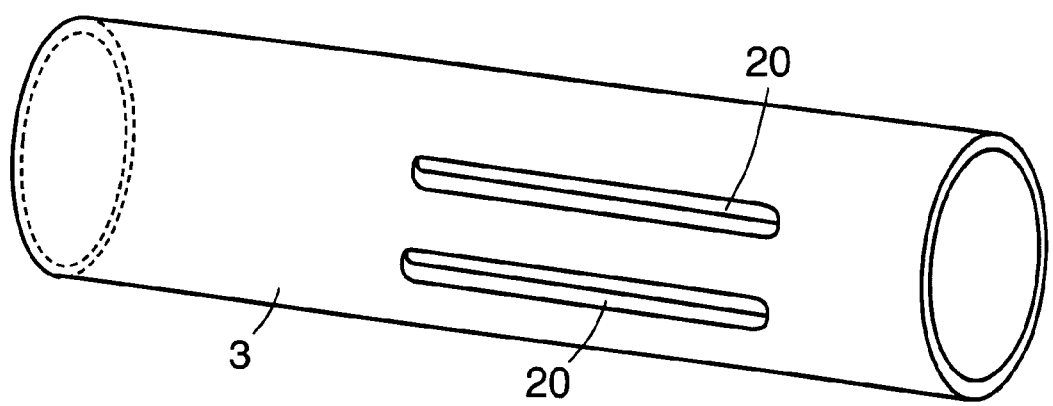
FIG. 6 is a side perspective view of the body tube.

FIG. 6 shows the body tube 3 which is an elongated Plexiglas™ tube having two elongated animal access slots 20. By turning to FIG. 12 it will be appreciated that body tube 3 may be slideably inserted through access hole 11 of the rear mounting plate 7 and into access hole 11 of body tube bracket 9. Once inserted, clamping screw 18 may be tightened to releasably secure the body tube 3 in the body tube bracket 9.

Figure 7:
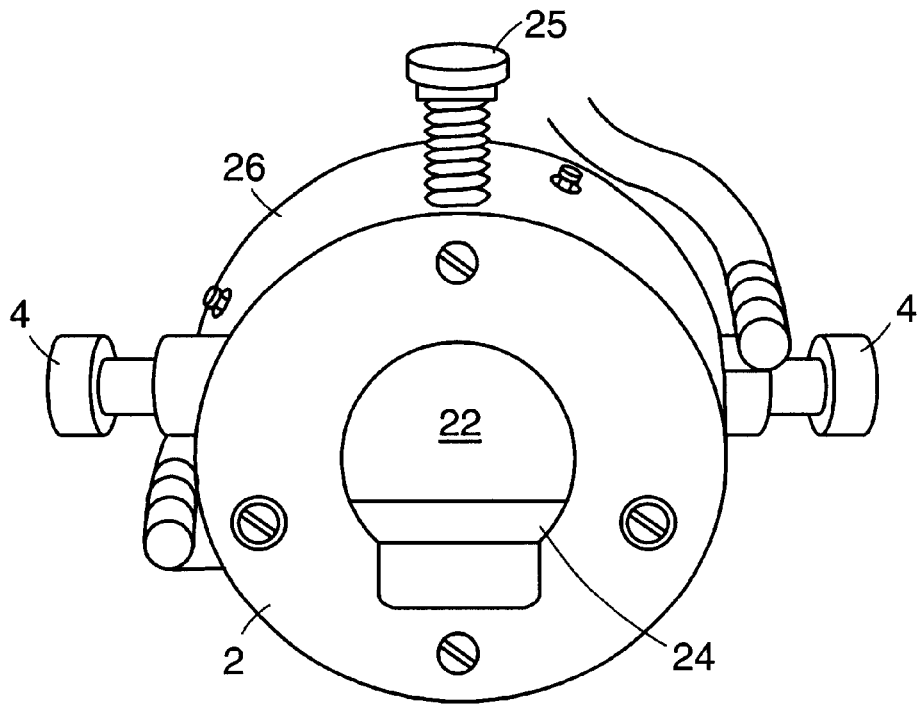
FIG. 7 is a front perspective view of the cylindrical head holder.
Figure 8:
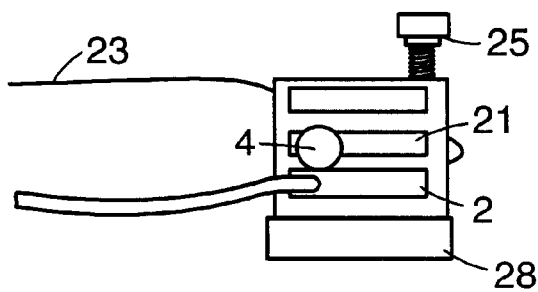
FIG. 8 is a side view of a rat in the cylindrical head holder.
Figure 9:
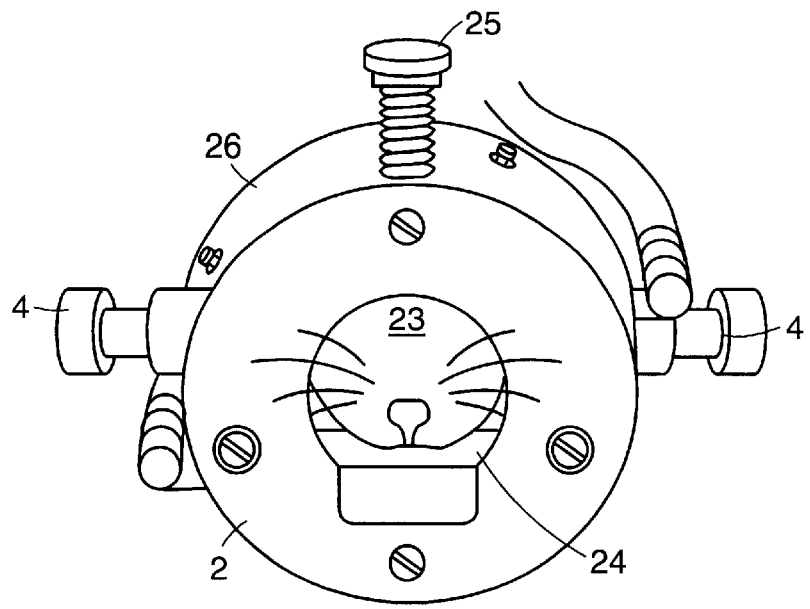
FIG. 9 is a front view of a rat in the cylindrical head holder.

FIGS. 7, 8 and 9 illustrate the head holder 2 having lateral ear clamping screws 4 inserted into lateral screw slots 21. The head holder 2 is a cylindrical tube having a central aperture 22 therethrough for receiving the head of an animal 23 and a bite bar 24 extending horizontally along a chord of the circular aperture 22 to provide a rest for the upper jaw of a restrained animal 23. Mounted through the top of the cylindrical head holder is a nose clamping screw 25 to secure the nose of a restrained animal 23 to the bite bar 24 as shown in FIG. 9. A pair of opposed lateral screw slots 21 are located in the sides of the cylindrical head holder to receive lateral ear clamping screws 4. Encompassing the head holder 2 is a birdcage coil 26. The head holder 2 is connected to the chassis 1 by a pair of mounting screws 29 (not shown) extending through the chassis 1 and into the head holder mount 28.

Figure 10:
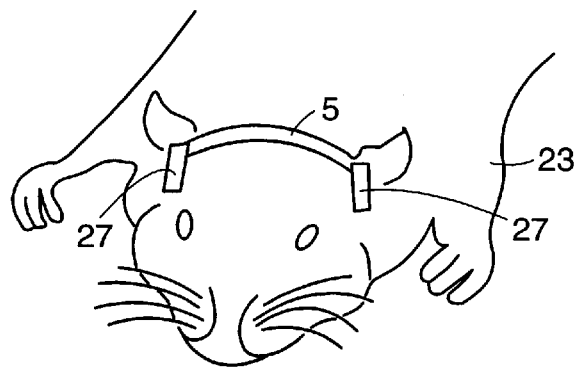
FIG. 10 is a front perspective view of a rat with the semi-circular ear piece.
Figure 11:
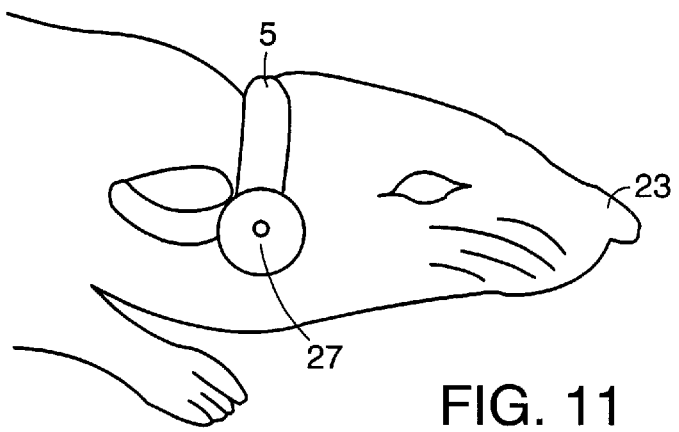
FIG. 11 is a side view of a rat with the semi-circular ear piece.

As shown in FIGS. 10 and 11, the semi-circular ear piece 5 is fitted over the head of the animal 23 whereupon the animal's head is placed into head holder 2. Lateral ear clamping screws 4 are inserted through a pair of lateral screw slots 21 and tightened against divots in a semi-circular ear piece 5 to prevent the animal from moving horizontally. The upper jaw of the animal 23 is fitted over the bite bar 24 and nose clamping screw 25 is tightened against the snout of the animal to secure it to the bite bar 24 and thereby eliminate vertical movement maintaining a stereotaxic position of the animal's head.

Figure 12:
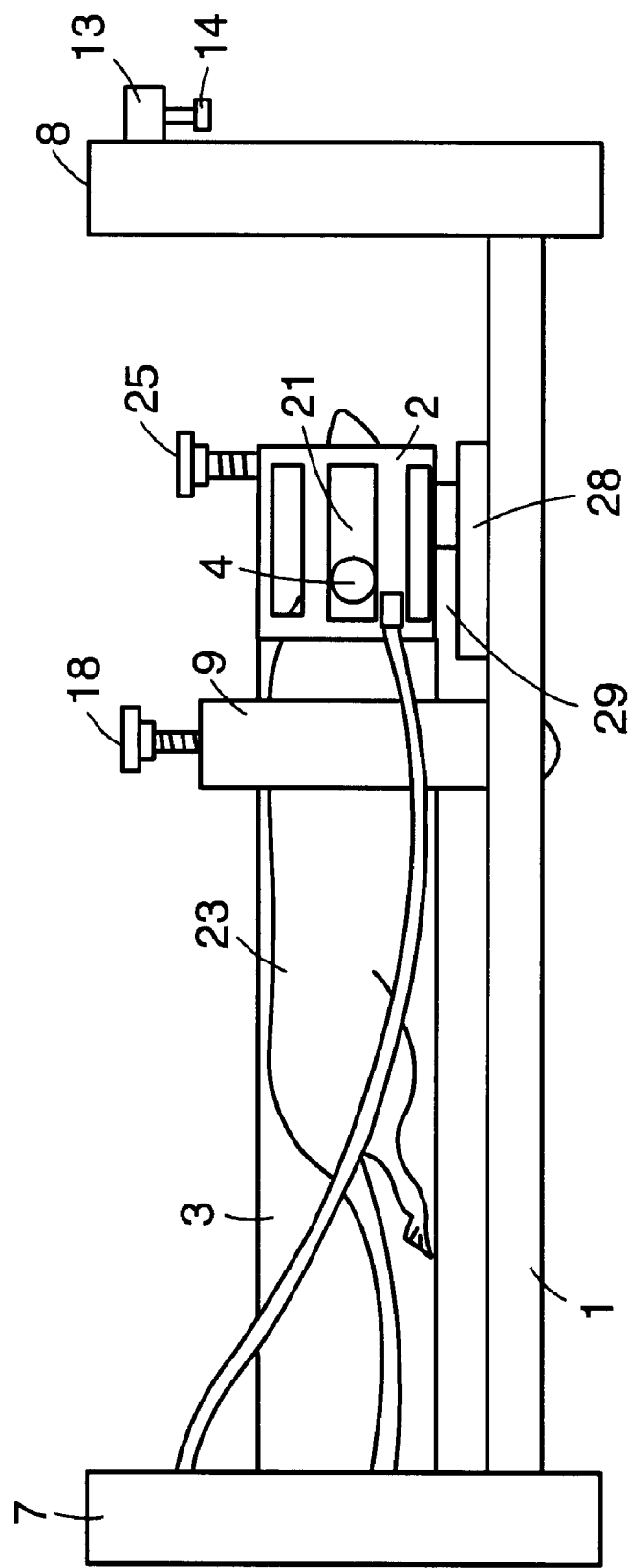
FIG. 12 is a side view of a rat in the assembled fMRI restraint.

As shown in FIG. 12, the cylindrical head holder is fixedly mounted to the chassis 1 by a pair of head holder mounting screws 29 threadably fastened into the head holder mount 28 allow adjustment of the cylindrical head holder 2 to properly fit different size animals. Once assembled the various components of the fMRI restraining assembly cooperate to minimize movement in an awake animal and thereby allows for a method of performing neuroimaging on an awake animal 23.

Turning now to FIG. 13 depicting a side perspective view of a second embodiment of the restraining assembly having an elongated rectangular chassis designated by the numeral 1, a Plexiglas™ head holder generally designated by the numeral 2, a Plexiglas™ body tube generally designated by the numeral 3, a rear mounting plate generally designated by the numeral 7, a front mounting plate generally designated by the numeral 8, and a body tube generally designated bracket by the numeral 9. The front mounting plate 8 has an access hole extending horizontally therethrough. Attached to the top front of the front mounting plate 8 is an assembly mounting block 13 and screw 14 and attached to the bottom front of the front mounting plate 8 is an anchor screw 30. The assembly mounting block 13 and the front anchor screw 30 are adapted to hold the assembly in place when inserted into the magnetic bore of a MRI tunnel. The front mounting plate 8 and rear mounting plate 7 each contain a chassis mounting slot 10 along the interior bottom to accept and interlock with the chassis 1.

A series of parallel opposing adjusting holes 6 are located approximately in the middle section of chassis 1. The head holder 2 connects to the chassis 1 through head holder mounting screw 29 and corresponding adjusting holes 6. The head holder 2 has a central generally circular aperture running horizontally therethrough and along the central axis of the chassis. The head holder 2 has a head clamping screw 31 located at the top front of the head holder 2 extending radially downward to the front of the head holder 2 and extends into the central aperture. The head holder 2 also has a nose clamping screw 25 at the top front of the head holder 2 extending radially downward to the rear of the head holder 2 and extends into the central aperture. The head holder 2 further has a pair of jaw screws 32 located at the bottom front of the head holder 2 and extending radially inward into the head holder's central aperture.

Ear clamping screws 4 are located on opposite sides of the head holder 2 within the lateral screw slots 21 and extend horizontally into the central axis of the chassis. The lateral screw slots 21 are located on opposite sides of the head holder 2 and extend from the rear edge of the head holder 2 toward the front of the head holder 2. The restrained animal wears a semi-circular ear piece 6 and soft rubber pads 36 to protect the animal's ear canals. The animal's head is fitted into the head holder 2 and the ear clamping screws 4, which slide into the lateral screw slots 21, fasten onto divots on the disk end portions of the semi-circular ear piece 6.

The body tube 3 is an elongated Plexiglas™ cylinder attached to the chassis 1 through a rear mounting plate 7 at the end of the chassis opposite the front mounting plate 8. An anchor screw 30 is located at the bottom rear of the rear mounting plate 7 that is adapted to hold the assembly in place when inserted into the magnetic bore of a MRI tunnel. The rear mounting plate 7 has an access hole running generally horizontally through the center to receive and align the body tube 3. The rear mounting plate 7 also contains a body tube clamp 33 located at the top of the rear mounting plate 7. The rear mounting plate 7 has a chassis mounting slot 10 along the bottom front to accept and interlock with the chassis 1. The rear mounting plate 7 further has a removable crown 34 to allow easier placement of the body tube 3 into rear mounting plate 7. The rear body tube clamp 33 acts to hold the crown in place.

The body tube bracket 9 is located along the chassis 1 between the head holder 2 and the rear mounting plate 7 and is adjustably attached to the chassis 1 by a pair of aligning screws 35 (not shown) in a corresponding adjusting holes 6. The body tube bracket 9 has an access hole running horizontally therethrough to receive and align the body tube 3. A clamping screw 18 and corresponding hole are located at the top of the body tube bracket 9 pointing downward to hold the body tube in place.

FIG. 14 describes a novel restraining jacket 37 used to restrain an animal. The jacket is made of a Velcro™ lined, non-flexible fabric with a Velcro™ closure 38. Arm and leg holders 39 and 40, respectively, further restrict the animal's movement. The jacket has holes for the animal's head 41 and 42, respectively.

The present invention demonstrates novel images of neuronal activation in conscious animals. Current methods utilizing anesthetized animals, which are known to exhibit dampened neuronal activity, may mask low signal levels. Furthermore, since the level of arousal (conscious vs. anesthetized) is inextricably linked to behavior, the future use of this assembly will be a significant step in providing a better understanding of the neural circuitry that facilitates behaviors such as responses to visual stimulation, temperature regulation, and motor stimulation, in addition to a range of different environmental stressors and interneurodevelopmental and intraneurodevelopmental studies. Therefore, researchers interested in the brain and/or behavior (utilizing laboratory animals) will be further assisted in their discoveries, with the utilization of this new assembly.

It will be appreciated that the above description contains many specificities, these should not be construed as limitations on the scope of the invention, but rather as an exemplification of a preferred embodiment thereof. Many other variations are possible.

What is claimed is:

1. A stereotaxic restraining assembly to immobilize a head and body of an awake animal for insertion into the tunnel bore of a magnetic resonance imaging (MRI) device, comprising:

a non-magnetic assembly adapted to be slidably mounted in said bore of said MRI device comprising
a chassis;
a first mounting plate at one end of said chassis, and having a hole extending therethrough;
a second mounting plate at a second end of said chassis opposite said first mounting plate, and having a hole extending therethrough;
an elongated body tube seated in said access hole through said second mounting plate and extending along said chassis, said tube being connected to said body tube bracket which connected to the second mounting plate, the body tube enclosing the awake animals arms and legs;
a head holder that restrains the head of an animal, the head holder having a rf coil and an aperture extending therethrough and a plurality of adjustable immobilizing components to secure an animal's head.

2. A stereotaxic restraining assembly in accordance with claim 1, wherein said head holder further comprises a pair of lateral ear clamping screws extending horizontally through the sides of said head holder into the bore of said aperture and generally perpendicular to the elongated axis thereof and above a horizontal bite bar and adapted to abut a protective ear piece and limit the horizontal movement of the animal.

3. A stereotaxic restraining assembly, in accordance with claim 2, wherein said head holder further comprises a nose clamping screw extending inward through the top of said head holder into the bore of said aperture and adapted to abut the nose of an animal above said bite bar and secure the animal's jaw thereon.

4. A stereotaxic restraining assembly, in accordance with claim 3, wherein said head holder further comprises a pair of jaw anchor screws extending inward through said head holder into the bore of said aperture.

5. A stereotaxic restraining assembly, in accordance with claim 4, wherein said head holder further comprises a head clamping screw located at the top of said head holder and extending inward through said head holder into the bore of said aperture.

6. A stereotaxic restraining assembly, in accordance with claim 2, further comprising ear pads wherein said ear pads are placed under said protective ear piece.

7. A stereotaxic restraining assembly, in accordance with claim 1, further comprising a restraining jacket for immobilizing the animal.

8. A method of conducting neuroimaging on an awake animal, comprising:

restraining an un-anesthetized animal having arms and legs that are positioned in an assembly slidably mounted in a bore of an MRI device including a chassis;

a front mounting plate located at one end of the chassis and having a hole extending therethrough;

rear mounting plate located at one end of the chassis opposite the front mounting plate, and having a hole therethrough;

an elongated body tube seated in the hole through the rear mounting plate and extending along the chassis, the tube having an end positioned at the rear mounting plate, the tube enclosing the arms and legs of the un-anesthetized animal;

a head holder to restrain the head of an animal the head holder having a rf coil and having an aperture extending therethrough; and conducting a functional MRI (fMRI) imaging procedure on the brain the unanesthetized animal.

9. A method of conducting enhanced neuroimaging on awake animals, in accordance with claim 8, further comprising the step of amplifying the sensitivity of low field strength magnets by implementing exogenous contrast agents, blood oxygenation-level-dependant contrast and radio frequency sequences.

10. A method of conducting enhanced neuroimaging on awake animals, in accordance with claim 9 further comprising the steps of:

obtaining a computerized histological representation of the fMRI; and a three dimensional digital map of the imaged brain from a computerized histological representation of the fMRI signal.

11. A method of conducting enhanced neuroimaging on awake animals, in accordance with claim 9, wherein the fMRI test is done using a real-time three dimensional functioning unit.

12. A method of conducting enhanced neuroimaging on awake animals, in accordance with claim 8, further comprising the steps of:

obtaining a computerized histological representation of the fMRI; and creating a three dimensional digital map of the imaged brain from a computerized histological representation of the fMRI signal.

13. A method of conducting enhanced neuroimaging on awake animals, in accordance with claim 8 wherein the fMRI test is done using a real-time three dimensional functioning unit.

14. Apparatus for restraining a conscious animal during a magnetic resonance imaging procedure comprising;

a head holder with which an animal's head is restrained;

a chassis slidably mounted within an MRI device on which the head holder is mounted; the chassis having a first end plate and a second end plate mounted thereon such that the animal's body is positioned between the first end plate and the second end plate; and a body tube in which the animal's body legs and arms are enclosed, the body tube being attached to the second end plate.

15. The apparatus of claim 14 further comprising an rf coil that is mounted on the head holder.

16. The apparatus of claim 14 further comprising a hole in the second end plate, the body tube having a size such that the body tube can be inserted through the hole.

17. The apparatus of claim 14 further comprising a clamp on the head holder that is secured to the animals head and a bite bar.

18. The apparatus of claim 14 further comprising a restraining jacket that restrains an unanesthetized animal during an imaging procedure.

* * * * *